United States Patent [19]

Hada et al.

[11] Patent Number: 5,714,625
[45] Date of Patent: Feb. 3, 1998

[54] CYANOOXIME SULFONATE COMPOUND

[75] Inventors: Hideo Hada, Hiratsuka; Tatsuya Hashiguchi, Chigasaki; Hiroshi Komano, Kanagawa-ken; Toshimasa Nakayama, Chigasaki, all of Japan

[73] Assignee: Tokyo Ohka Kogyo Co., Ltd., Kawasaki, Japan

[21] Appl. No.: 712,884

[22] Filed: Sep. 12, 1996

[30] Foreign Application Priority Data

Sep. 29, 1995 [JP] Japan ................................. 7-254214

[51] Int. Cl.$^6$ ................................................. C07C 255/35
[52] U.S. Cl. ................................................. 558/437
[58] Field of Search ............................................... 558/437

[56] References Cited

U.S. PATENT DOCUMENTS

| | | | |
|---|---|---|---|
| 4,540,598 | 9/1985 | Berner et al. | 427/54.1 |
| 4,736,055 | 4/1988 | Dietliker et al. | 560/13 |
| 5,019,488 | 5/1991 | Mammato et al. | 430/325 |
| 5,216,135 | 6/1993 | Urano et al. | 534/556 |

FOREIGN PATENT DOCUMENTS

| | | |
|---|---|---|
| 0 044 115 | 1/1982 | European Pat. Off. . |
| 0 241 423 | 10/1987 | European Pat. Off. . |
| 0 361 907 | 4/1990 | European Pat. Off. . |
| 0 571 330 | 11/1993 | European Pat. Off. . |

Primary Examiner—Johann Richter
Assistant Examiner—Ebenezer Sackey
Attorney, Agent, or Firm—Wenderoth, Lind & Ponack

[57] ABSTRACT

Disclosed is a class of novel cyanooxime sulfonate compounds represented by the general formula $$NC-CR^1=N-O-SO_2-R^2,$$

in which $R^1$ and $R^2$ are, each independently from the other, an unsubstituted or halogen-substituted monovalent aliphatic hydrocarbon group selected from the group consisting of alkyl, cycloalkyl, alkenyl and cycloalkenyl groups. The group $R^1$ is preferably a cycloalkenyl group, e.g. 1-cyclopentenyl or 1-cyclohexenyl group, and $R^2$ is preferably a lower alkyl group having 1 to 4 carbon atoms. The compound releases an acid by the irradiation with ultraviolet light and is useful as an acid generating agent in an acid-sensitive photoresist composition. By virtue of the high transparency of the compound to ultraviolet, high acid strength of the acid generated therefrom and good solubility of the compound in organic solvents, the photoresist composition compounded with the compound as an acid generating agent is imparted with high sensitivity to ultraviolet and capable of giving a patterned resist layer having excellent characteristics.

6 Claims, No Drawings

CYANOOXIME SULFONATE COMPOUND

BACKGROUND OF THE INVENTION

The present invention relates to a novel cyanooxime sulfonate compound or, more particularly, relates to a non-aromatic cyanooxime sulfonate compound having usefulness as an acid generating agent in a photoresist composition.

Various kinds of oxime sulfonate compounds have been proposed and used in the prior art as an acid generating agent capable of releasing an acid by the irradiation with actinic rays in an acid-curable photoresist composition. For example, European Patent Publication EP 0 044 115 A1 discloses a heat-curable coating composition containing an acid-curable amino resin and an oxime sulfonate compound. Japanese Patent Kokai 60-65072 teaches a method for curing a baking-curable coating composition containing an acid-curable resin and an oxime sulfonate compound by the irradiation with a short-wavelength light. Japanese Patent Kokai 61-251652 discloses an oxime sulfonate compound having a substituent group such as an ethylenically unsaturated polymerizable group, epoxy group, hydroxy group and the like as well as a polymer thereof. Japanese Patent Kokai 1-124848 discloses a method for image patterning by the use of a composition comprising a film-forming organic resin and a photosensitive compound having an oxime sulfonate group and an aromatic group in the molecule. Japanese Patent Kokai 2-154266 discloses a photoresist composition comprising an alkali-soluble resin, oxime sulfonate compound and sensitivity-enhancing crosslinking agent. Japanese Patent Kokai 2-161444 teaches a method for the formation of a negative pattern by the use of an oxime sulfonate compound. Japanese Patent Kokai 6-67433 discloses a photoresist composition containing an oxime sulfonate compound for curing by the irradiation with the i-line ultraviolet light.

While a variety of oxime sulfonate compounds are disclosed in the above mentioned prior art documents, some of them have a cyano group —CN substituting at the oxime carbon including those shown below and named as a derivative of acetonitrile:

(1) α-(p-toluenesulfonyloxyimino)-α-phenyl acetonitrile of the formula

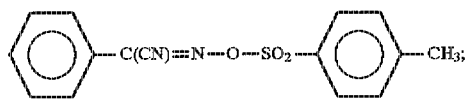

(2) α-(4-chlorobenzenesulfonyloxyimino)-α-phenyl acetonitrile of the formula

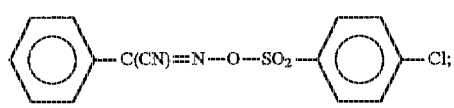

(3) α-(4-nitrobenzenesulfonyloxyimino)-α-phenyl acetonitrile of the formula

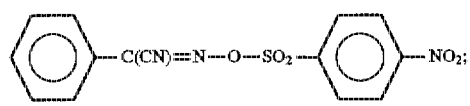

(4) α-(4-nitro-2-trifluoromethylbenzenesulfonyloxyimino)-α-phenyl acetonitrile of the formula

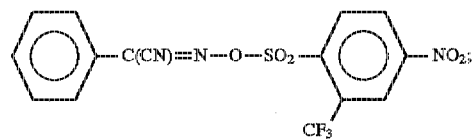

(5) α-(benzenesulfonyloxyimino)-α-(4-chlorophenyl) acetonitrile of the formula

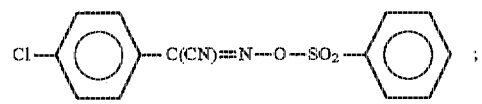

(6) α-(benzenesulfonyloxyimino)-α-(2,4-dichlorophenyl) acetonitrile of the formula

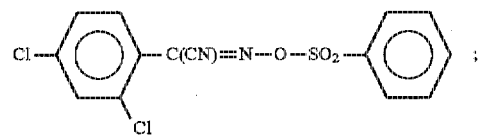

(7) α-(benzenesulfonyloxyimino)-α-(2,6-dichlorophenyl) acetonitrile of the formula

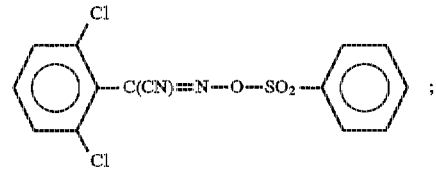

(8) α-(benzenesulfonyloxyimino)-α-(4-methoxyphenyl) acetonitrile of the formula

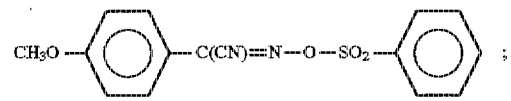

(9) α-(2-chlorobenzenesulfonyloxyimino)-α-(4-methoxyphenyl) acetonitrile of the formula

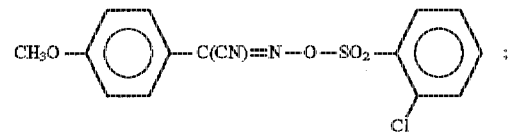

(10) α-(benzenesulfonyloxyimino)-α-(2-thienyl) acetonitrile of the formula

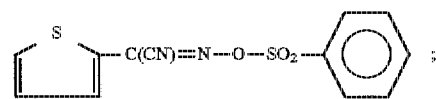

(11) α-(4-dodecylbenzenesulfonyloxyimino)-α-phenyl acetonitrile of the formula

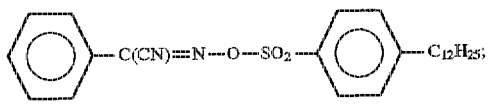

(12) α-(p-toluenesulfonyloxyimino)-α-(4-methoxyphenyl) acetonitrile of the formula

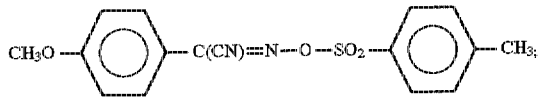

(13) α-(4-dodecylbenzenesulfonyloxyimino)-α-(4-methoxyphenyl) acetonitrile of the formula

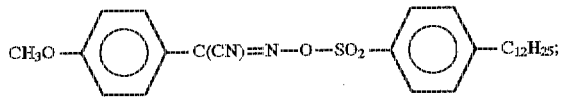

and

(14) α-(p-toluenesulfonyloxyimino)-α-(3-thienyl) acetonitrile of the formula

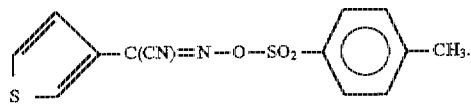

As is shown above, it is a remarkable fact that each of the oxime sulfonate compounds having a cyano group known in the prior art also has an aromatic group such as phenyl group, thienyl group and the like.

As is known, phenyl groups as a typical example of the aromatic substituent groups have strong absorption of the ultraviolet light having a wavelength of 248 nm, which is the wavelength of the KrF laser beam frequently used for the pattern-wise exposure of the photoresist layer, so that a photoresist composition containing an oxime sulfonate compound having a phenyl group has a problem that the ultraviolet light is largely absorbed in the resist layer resulting in a decrease in the intensity of the light reaching the bottom of the resist layer in contact with the substrate surface. As a consequence, the cross sectional profile of the line-wise patterned resist layer obtained by development cannot be orthogonal but is trapezoidal with a larger width at the bottom when the photoresist composition is positive-working or inversely trapezoidal with a smaller width at the bottom when the photoresist composition is negative-working. Patterning of contact holes also has a problem of a decrease in the focusing depth latitude due to the low transmissivity of the ultraviolet light through the photoresist layer.

In view of the above described problem in the photoresist compositions due to the low ultraviolet transmissivity through the photoresist layer containing an oxime sulfonate compound with an aromatic group, alternatively, Japanese Patent Kokai 4-210960 proposes use of bis (cyclohexylsulfonyl) diazomethane as an acid generating agent in a photoresist composition free of the problem of ultraviolet absorption. This compound, however, is defective because, though with high transmissivity to ultraviolet light, the acid generated therefrom has a relatively low acid strength so that the sensitivity of the photoresist composition containing the compound cannot be high enough in addition to the problem of low heat resistance of the resist layer formed from the composition.

Besides, the oxime sulfonyl or sulfonate compounds having aromatic groups known in the prior art in general have problems that, when used as an acid generating agent in a photoresist composition, the cross sectional profile of the patterned resist layer is sometimes wavy and, due to their low solubility in an organic solvent used in the preparation of the photoresist composition, the amount thereof contained in the photoresist composition is so limited that the sensitivity of the photoresist composition cannot be high enough or the compound as the acid generating agent can be dissolved in the photoresist composition only by undertaking an additional step of heating resulting in an increase in the costs for the preparation of the photoresist compositions.

SUMMARY OF THE INVENTION

The present invention accordingly has a primary object to provide a novel acid generating agent in a photoresist composition free from the above described problems and disadvantages in the conventional acid generating agents.

The investigations undertaken by the inventors to accomplish the above described primary object have led to an unexpected discovery that non-aromatic cyanooxime sulfonate compounds, as a class of novel compounds not known in the prior art nor described in any literatures, well meet the above mentioned primary object of the invention.

Thus, the non-aromatic cyanooxime sulfonate compound provided by the invention is a compound represented by the general formula $$NC-CR^1=N-O-SO_2-R^2, \qquad (I)$$

in which $R^1$ and $R^2$ are, each independently from the other, an unsubstituted or halogen-substituted monovalent aliphatic hydrocarbon group selected from the group consisting of alkyl, cycloalkyl, alkenyl and cycloalkenyl groups.

Among the non-aromatic cyanooxime sulfonate compounds falling within the above given definition of the compound, particularly useful compounds as an acid generating agent in a photoresist composition include those of which the group denoted by $R^1$ in the general formula is a cycloalkenyl group, preferably, such as cyclopentenyl and cyclohexenyl groups and the group denoted by $R^2$ is an alkyl group, preferably, having 1 to 4 carbon atoms.

DETAILED DESCRIPTION OF THE PREFERRED EMBODIMENTS

As is described above, the novel compound provided by the invention is a cyanooxime sulfonate compound represented by the above given general formula (I), which is free from any aromatic groups including those having a benzene ring, naphthalene ring, furan ring, thiophene ring, pyridine ring and the like.

Namely, the groups denoted by $R^1$ and $R^2$ in the general formula (I) are each an unsubstituted or halogen-substituted monovalent aliphatic hydrocarbon group selected from the group consisting of alkyl, alkenyl, cycloalkyl and cycloalkenyl groups. The alkyl and alkenyl groups can be straightly linear or branched and preferably have 12 carbon atoms or less as exemplified by methyl, ethyl, n-propyl, isopropyl, n-butyl, sec-butyl, tert-butyl, n-pentyl, n-octyl and n-dodecyl groups as the examples of the alkyl groups and ethenyl, propenyl, butenyl, butadienyl, hexenyl and octadienyl groups as the examples of the alkenyl groups. The cycloalkyl and cycloalkenyl groups should preferably have 4 to 12 carbon atoms as exemplified by cyclopentyl, cyclohexyl, cyclooctyl and cyclododecyl groups as the examples of the cycloalkyl groups and 1-cyclobutenyl, 1-cyclopentenyl, 1-cyclohexenyl, 1-cycloheptenyl and 1-cyclooctenyl groups as the examples of the cycloalkenyl groups.

The above named aliphatic hydrocarbon groups can be substituted by an atom of halogen such as chlorine, bromine and fluorine for one or more of the hydrogen atoms therein or, namely, can be halogenated aliphatic hydrocarbon groups. Examples of a halogenated aliphatic hydrocarbon group having, in particular, 1 to 4 carbon atoms include chloromethyl, trichloromethyl, trifluoromethyl and 2-bromopropyl groups.

The above defined oxime sulfonate compound of the present invention represented by the general formula (I) has relatively high transmissivity to the actinic rays or, in particular, far ultraviolet light used in the pattern-wise exposure of a photoresist layer so that, when the compound is used as an acid generating agent in a photoresist composition, advantages can be obtained that improvements are accomplished in the orthogonality in the cross sectional profile of the patterned resist layer and the focusing-depth latitude in the pattern-wise exposure of the photoresist layer to light.

While it is a problem in the prior art that introduction of cyclohexyl groups into the sulfonyl diazomethane compound to give bis(cyclohexylsulfonyl) diazomethane conventionally used as an acid generating agent in a photoresist composition generates an acid of a relatively low acid strength resulting in a decrease of the photosensitivity of the composition and a decrease in the heat resistance of the patterned resist layer, it is a quite unexpected discovery that the photoresist composition compounded with the inventive cyanooxime sulfonate compound is free from such disadvantages. The mechanism therefor is, though not well understood, presumably due to the cyano-substituted oxime group in the compound. It is preferable, from the standpoint of obtaining high photosensitivity of the photoresist composition, that the group denoted by $R^2$ in the general formula (I) is selected from the group consisting of lower alkyl groups having 1 to 4 carbon atoms such as methyl, ethyl, n-propyl, isopropyl and butyl groups, trichloromethyl group, trifluoromethyl group and cyclohexyl group.

The solubility of the inventive cyanooxime sulfonate compound in an organic solvent used in the preparation of a photoresist composition can be greatly increased by selecting the group denoted by $R^1$ in the general formula (I) from alkyl, cycloalkyl and cycloalkenyl groups so that advantages are obtained that the photoresist composition can be prepared without heating to dissolve the acid generating agent in an organic solvent and the amount of the acid generating agent formulated in the composition is free from the limitations due to the low solubility of the acid generating agent in an organic solvent consequently to ensure high photosensitivity of the photoresist composition. From the standpoint of obtaining a high solubility of the inventive cyanooxime sulfonate compound in an organic solvent, the group denoted by $R^1$ is selected preferably from the group consisting of lower alkyl groups having 1 to 4 carbon atoms such as ethyl, propyl and butyl groups, cyclopentyl group, cyclohexyl group, 1-cyclobutenyl group, 1-cyclopentenyl group, 1-cyclohexenyl group and 1-cycloheptenyl group.

While a photoresist composition compounded with the conventional oxime sulfonate compound disclosed in the above mentioned prior art documents generally has a problem that the patterning work with the photoresist composition is under the influences of standing waves resulting in appearance of a wavy side lines of the cross sectional profile of the patterned resist layer, it is also an unexpected discovery that the photoresist composition compounded with the inventive cyanooxime sulfonate compound is free from such an adverse influence of standing waves to decrease the waviness of the cross sectional profile of the patterned resist layer. The reason therefor is presumably that the substituent groups denoted by $R^1$ and $R^2$ in the inventive oxime sulfonate compound have an effect to promote diffusion of the acid generated from the compound by the pattern-wise irradiation of the photoresist layer with actinic rays in the course of the heat treatment to follow the pattern-wise exposure to actinic rays.

From the standpoint of obtaining an orthogonal cross sectional profile of the patterned resist layer without waviness insusceptibly to the influences of standing waves, the group denoted by $R^2$ is selected preferably from the group consisting of lower alkyl groups having 1 to 4 carbon atoms such as methyl, ethyl, n-propyl, isopropyl and butyl groups, trichloromethyl group, trifluoromethyl group and cyclohexyl group.

When the above mentioned various requirements are taken into consideration for the inventive cyanooxime sulfonate compound to be used as an acid generating agent in a photoresist composition, it is preferable that the groups denoted by $R^1$ and $R^2$ are a cycloalkenyl group and an alkyl group, respectively, or, more preferably, cyclopentenyl or cyclohexenyl group and a lower alkyl group having 1 to 4 carbon atoms, respectively.

The cyano-substituted oxime sulfonate compound of the present invention can be synthesized according to a procedure which is a modification of the synthetic procedure described in the above given prior art documents. For example, a cyano-substituted oxime group-containing compound of the formula $R^1$—C(CN)=N—OH and a sulfonyl chloride group-containing compound of the formula Cl—$SO_2$—$R^2$ are subjected to a dehydrochlorination reaction according to the reaction equation $$R^1\text{---}C(CN)\text{=}N\text{---}OH + Cl\text{---}SO_2\text{---}R^2 \rightarrow R^1\text{---}C(CN)\text{=}N\text{---}O\text{---}SO_2\text{---}R^2 + HCl,$$

in which each symbol has the same meaning as defined above, in an organic solvent such as tetrahydrofuran, N,N-dimethyl formamide, N,N-dimethyl acetamide, N-methyl pyrrolidone and the like in the presence of a basic catalyst or an acid acceptor such as pyridine, triethylamine and the like. The cyano-substituted oxime group-containing compound as one of the starting reactants can be prepared by a known method such as those disclosed in The Systematic Identification of Organic Compounds, page 181 (1980, John Wiley & Sons), Die Makromolekulare Chemie, volume 108, page 170 (1967) and Organic Syntheses, volume 59, page 95 (1979).

Some of the examples of the compounds which can be prepared by the above described synthetic procedure include:

α-(methylsulfonyloxyimino)-1-cyclopentenyl acetonitrile;
α-(methylsulfonyloxyimino)-1-cyclohexenyl acetonitrile;
α-(ethylsulfonyloxyimino)-1-cyclopentenyl acetonitrile;
α-(isopropylsulfonyloxyimino)-1-cyclopentenyl acetonitrile;
α-(n-butylsulfonyloxyimino)-1-cyclopentenyl acetonitrile;
α-(ethylsulfonyloxyimino)-1-cyclohexenyl acetonitrile;

α-(isopropylsulfonyloxyimino)-1-cyclohexenyl acetonitrile; and α-(n-butylsulfonyloxyimino)-1-cyclohexenyl acetonitrile.

When the cyano-substituted oxime sulfonate compound of the invention is to be used as an acid generating agent in a photoresist composition, the compound is dissolved in an organic solvent together with a film-forming resinous ingredient to give the desired photoresist composition. The amount of the inventive compound in such a photoresist composition is usually in the range from 1 to 30 parts by weight per 100 parts by weight of the film-forming resinous ingredient.

The cyano-substituted oxime sulfonate compound is a novel compound not known in the prior art nor described in any literatures and has usefulness as an acid generating agent in a photoresist composition. The advantages obtained by the use of the inventive compound as an acid generating agent in a photoresist composition include: (1) high transparency of the composition to far ultraviolet light used in the pattern-wise exposure of the photoresist layer consequently with excellent orthogonality of the cross sectional profile of the patterned resist layer as well as good focusing depth characteristics; (2) high acid strength of the acid generated therefrom by the irradiation with actinic rays consequently with excellent photosensitivity of the resist composition and heat resistance of the patterned resist layer; (3) excellent solubility of the compound in an organic solvent used in the preparation of the photoresist composition so as to enhance the sensitivity of the composition by virtue of an increase in the amount of the acid generating compound, which can be dissolved in a solvent even without heating; and (4) reduction of the adverse influences by the standing waves so as to prevent appearance of a wavy contour of the patterned resist layer.

In the following, the cyano-substituted oxime sulfonate compound of the invention is illustrated in more detail by way of examples for the synthetic preparation and characterization thereof followed by a description of the application thereof as an acid generating agent in a photoresist composition.

The term of "parts" in the following always refers to "parts by weight".

EXAMPLE 1

A reaction mixture was prepared from 64.5 g of methyl alcohol, 365 g of xylene, 80 g (2 moles) of sodium hydroxide and 107 g (1 mole) of 1-cyclopentenyl acetonitrile and, while keeping the reaction mixture in a vessel at a temperature of 40° C., 125 g (1.07 moles) of isopentyl nitrito were added dropwise thereinto taking 2 hours followed by further continued agitation of the mixture for additional 2 hours at the same temperature and then for 20 hours at room temperature. Thereafter, the reaction mixture was diluted and emulsified by the addition of water and the pH of the emulsion was adjusted to 14 by the use of an aqueous solution of sodium hydroxide. The emulsion was destroyed by standing and separated into the aqueous and organic phases. After discarding the organic phase, the aqueous phase was acidified with hydrochloric acid followed by extraction of the reaction product contained therein with diethyl ether. The ether solution thus obtained was dehydrated and subjected to evaporation of the ether to give a solid residue which was recrystallized from a toluene solution to give 120 g of a purified product which could be identified to be α-hydroxyimino-1-cyclopentenyl acetonitrile from the analytical results shown below. The above mentioned yield of the product was 88.5% of the theoretical value.

The infrared absorption spectrum of this product compound had absorption bands with peaks at wave numbers of 1294 $cm^{-1}$, 1363 $cm^{-1}$, 1614 $cm^{-1}$, 2244 $cm^{-1}$ and 3317 $cm^{-1}$. The proton nuclear magnetic resonance ($^1$H-NMR) absorption spectrum of the compound measured in heavy methyl alcohol $CD_3OD$ as the solvent had peaks of the δ value at 2.02 ppm, 2.50 to 2.60 ppm, 4.89 ppm and 6.35 ppm. These results supported the above mentioned identification of the compound.

Into a solution prepared by dissolving 39.4 g (0.29 mole) of the above obtained α-hydroxyimino-1-cyclopentenyl acetonitrile in 400 ml of tetrahydrofuran containing 44.0 g (0.43 mole) of triethylamine and kept at −5° C. were introduced dropwise 36.5 g (0.32 mole) of mesyl chloride over a period of 2 hours followed by agitation of the mixture at the same temperature for 3 hours and then at about 10° C. for 2 hours. The reaction mixture was freed from tetrahydrofuran by evaporation at 30° C. under reduced pressure to give a crude reaction product which was subjected to purification. Thus, a 60 g portion of the crude product was subjected to several times of recrystallization from an acetonitrile solution to give 35 g of a white crystalline compound having a melting point of 96° C. as the final product which could be identified from the following analytical results to be α-(methylsulfonyloxyimino)-1-cyclopentenyl acetonitrile. The above mentioned yield of the final product corresponds to 50.4% of the theoretical value.

The infrared absorption spectrum of this product compound had absorption bands with peaks at wave numbers of 1189 $cm^{-1}$, 1376 $cm^{-1}$, 1610 $cm^{-1}$, 2242 $cm^{-1}$ and 2940 $cm^{-1}$. The $^1$H-NMR absorption spectrum of the compound measured in heavy chloroform $CDCl_3$ as the solvent had peaks of the δ value at 2.10 ppm, 2.64 to 2.70 ppm, 3.26 ppm and 6.90 ppm. These results supported the above mentioned identification of the compound. Further, the ultraviolet absorption spectrum of the compound was measured in propyleneglycol monomethyl ether as the solvent to detect absorption bands having peak wavelengths at 214.5 nm and 278.5 nm with molar absorption coefficients of ε=6010 and ε=10600, respectively. The molar absorption coefficient ε at a wavelength of 248 nm was 1500 indicating high transmissivity to the KrF laser beam conventionally used in the pattern-wise exposure of the photoresist layer.

The solubility behavior of the above obtained compound was tested in propyleneglycol monomethyl ether acetate as the solvent by estimating the length of time taken for the preparation of a clear 1% by weight solution at room temperature under agitation to find that the solution was clear enough after about 1 minute of agitation while the length of time was about 10 minutes and about 5 minutes for bis(cyclohexylsulfonyl) diazomethane and α-(p-toluenesulfonyloxyimino)-4-methoxyphenyl acetonitrile, respectively.

APPLICATION EXAMPLE 1

A positive-working photoresist composition was prepared by dissolving, in 500 parts of propyleneglycol monomethyl ether acetate, 30 parts of a first polyhydroxystyrene substituted by tert-butoxycarbonyloxy groups for 39% of the hydroxy groups and having a weight-average molecular weight of 10000, 70 parts of a second polyhydroxystyrene substituted by ethoxyethoxy groups for 39% of the hydroxy groups and having a weight-average molecular weight of 10000, 3 parts of the α-(methylsulfonyloxyimino)-1-cyclopentenyl acetonitrile prepared in Example 1 described above, 0.1 part of triethylamine, 0.2 part of salicylic acid and 2 parts of N,N-dimethylacetamide followed by filtration of the solution through a membrane filter of 0.2 μm pore diameter.

This photoresist solution was applied to the surface of a silicon wafer on a spinner followed by drying on a hot plate at 90° C. for 90 seconds to form a dried photoresist layer having a thickness of 0.7 μm, which was exposed patternwise on a minifying projection exposure machine (Model NSR-2005EX8A, manufactured by Nikon Co.) in doses stepwise increased with increments of each 1 mJ/cm$^2$ by varying the exposure time followed by a post-exposure baking treatment at 110° C. for 90 seconds and developed with a 2.38% by weight aqueous solution of tetramethylammonium hydroxide at 23° C. for 65 seconds followed by rinse with water for 30 seconds and drying. Recording was made there for the minimum exposure dose in mJ/cm$^2$, which was 4 mJ/cm$^2$ in this case, as a measure of the sensitivity by which the resist layer in the exposed areas was completely dissolved away in the development treatment.

Further, a scanning electron microscopic photograph was taken of the cross sectional profile of the patterned resist line of 0.23 μm width to find that the cross sectional profile was excellently orthogonal standing upright on the substrate surface without waviness. The focusing-depth latitude around a contact hole of 0.3 μm diameter was 1.6 μm. Heat resistance of the thus formed patterned resist layer was examined by heating the silicon wafer not to detect any slight deformation of the edges of the patterned resist line even by heating at 130° C.

For comparison, the same testing procedure as above was repeated excepting replacement of the α-(methylsulfonyloxyimino)-1-cyclopentenyl acetonitrile as the acid generating agent with the same amount of α-(p-toluenesulfonyloxyimino)-4-methoxyphenyl acetonitrile. The results were that the sensitivity was 6 mJ/cm$^2$, the cross sectional profile of the line-patterned resist layer of 0.23 μm width was trapezoidal with waviness due to the influences of standing waves and the focusing-depth latitude around a contact hole of 0.3 μm diameter was 1.2 μm although the heat resistance of the patterned resist layer was about equivalent to that with the inventive compound as the acid generating agent.

For further comparison, the same testing procedure as above was repeated excepting replacement of the α-(methylsulfonyloxyimino)-1-cyclopentenyl acetonitrile as the acid generating agent with the same amount of bis(cyclohexylsulfonyl)diazomethane. The results were that the sensitivity was 30 mJ/cm$^2$, the cross sectional profile of the line-patterned resist layer of 0.23 μm width was orthogonal standing upright on the substrate surface without waviness, the focusing-depth latitude around a contact hole of 0.3 μm diameter was 1.6 μm and the heat resistance of the patterned resist layer was inferior to show collapsing of the edges of a line-patterned resist layer by heating at 125° C.

APPLICATION EXAMPLE 2

A negative-working photoresist composition was prepared by dissolving, in 650 parts of propyleneglycol monomethyl ether, 100 parts of a copolymer of styrene and hydroxystyrene having a weight-average molecular weight of 2500, 10 parts of a urea resin (Mx-290, a product by Sanwa Chemical Co.), 0.3 part of a melamine resin (Mx-750, a product by Sanwa Chemical Co.) and 8.9 parts of the α-(methylsulfonyloxyimino)-1-cyclopentenyl acetonitrile prepared in Example 1 described above.

This photoresist solution was applied to the surface of a silicon wafer on a spinner followed by drying on a hot plate at 100° C. for 90 seconds to form a dried photoresist layer having a thickness of 0.7 μm, which was exposed patternwise to an excimer laser beam on a minifying projection exposure machine (Model NSR-2005EX8A, manufactured by Nikon Co.) followed by a post-exposure baking treatment at 130° C. for 90 seconds and developed with a 2.38% by weight aqueous solution of tetramethylammonium hydroxide at 23° C. for 65 seconds followed by rinse with water for 30 seconds and drying. Recording was made there for the minimum exposure dose in mJ/cm$^2$, which was 1 mJ/cm$^2$ in this case, as a measure of the sensitivity by which incipient pattern formation could be detected on the exposed areas of the resist layer in the development treatment.

For comparison, the same testing procedure as above was repeated excepting replacement of the α-(methylsulfonyloxyimino)-1-cyclopentenyl acetonitrile as the acid generating agent with the same amount of tris(2,3-dibromopropyl) isocyanurate to find that the sensitivity was 20 mJ/cm$^2$.

EXAMPLE 2

A reaction mixture was prepared from 64.5 g of methyl alcohol, 365 g of xylene, 80 g (2 moles) of sodium hydroxide and 121 g (1 mole) of 1-cyclohexenyl acetonitrile and, while keeping the reaction mixture in a vessel at a temperature of 40° C., 125 g (1.07 moles) of isopentyl nitrito were added dropwise thereinto taking 2 hours followed by further continued agitation of the mixture for additional 2 hours at the same temperature and then for 20 hours at room temperature. Thereafter, the reaction mixture was diluted and emulsified by the addition of water and the pH of the emulsion was adjusted to 14 by the use of an aqueous solution of sodium hydroxide. The emulsion was destroyed by standing and separated into the aqueous and organic phases. After discarding the organic phase, the aqueous phase was acidified with hydrochloric acid followed by extraction of the reaction product contained therein with diethyl ether. The ether solution thus obtained was dehydrated and subjected to evaporation of the ether to give a solid residue which was recrystallized from a toluene solution to give 105 g of a purified product which could be identified to be α-hydroxyimino-1-cyclohexenyl acetonitrile from the analytical results shown below. The above mentioned yield of the product was 70.2% of the theoretical value.

The infrared absorption spectrum of this product compound had absorption bands with peaks at wave numbers of 1033 cm$^{-1}$, 1633 cm$^{-1}$, 2237 cm$^{-1}$, 2931 cm$^{-1}$ and 3347 cm$^{-1}$. The proton nuclear magnetic resonance ($^1$H-NMR) absorption spectrum of the compound measured in heavy chloroform CDCl$_3$ as the solvent had peaks of the δ value at 1.66 ppm, 2.27 ppm and 6.55 ppm. These results supported the above mentioned identification of the compound.

Into a solution prepared by dissolving 43.5 g (0.29 mole) of the above obtained α-hydroxyimino-1-cyclohexenyl acetonitrile in 400 ml of tetrahydrofuran containing 44.0 g (0.43 mole) of triethylamine kept at −5° C. were introduced dropwise 36.5 g (0.32 mole) of mesyl chloride over a period of 2 hours followed by agitation of the mixture at the same temperature for 3 hours and then at about 10° C. for 2 hours. The reaction mixture was freed from tetrahydrofuran by evaporation at 30° C. under reduced pressure to give a crude reaction product which was subjected to purification. Thus, a 60 g portion of the crude product was subjected to several times of recrystallization from an acetonitrile solution to give 16.9 g of a white crystalline compound having a melting point of 72° C. as the final product which could be identified from the following analytical results to be α-(methylsulfonyloxyimino)-1-cyclohexenyl acetonitrile. The above mentioned yield of the final product mentioned above corresponds to 25.6% of the theoretical value.

The infrared absorption spectrum of this product compound had absorption bands with peaks at wave numbers of 840 cm$^{-1}$, 1189 cm$^{-1}$, 1629 cm$^{-1}$, 2240 cm$^{-1}$ and 2940 cm$^{-1}$. The $^1$H-NMR absorption spectrum of the compound measured in heavy chloroform CDCl$_3$ as the solvent had peaks of the δ value at 1.70 ppm, 2.37 ppm, 3.22 ppm and 6.90 ppm. These results supported the above mentioned identification of the compound. Further, the ultraviolet absorption spectrum of the compound was measured in propyleneglycol monomethyl ether as the solvent to detect absorption bands having peak wavelengths at 212 nm and 272 nm with molar absorption coefficients of ε=5700 and ε=11600, respectively. The molar absorption coefficient at a wavelength of 248 nm was 2500 indicating high transmissivity to the KrF laser beam.

The solubility behavior of the compound in propyleneglycol monomethyl ether acetate was as good as that of the compound prepared in Example 1.

EXAMPLE 3

α-(Ethylsulfonyloxyimino)-1-cyclopentenyl acetonitrile having a melting point of 90° C. was prepared in substantially the same manner as in Example 1 excepting replacement of the mesyl chloride with the same molar amount of ethanesulfonyl chloride.

The infrared absorption spectrum of this product compound had absorption bands with peaks at wave numbers of 894 cm$^{-1}$, 970 cm$^{-1}$, 1376 cm$^{-1}$, 1610 cm$^{-1}$ and 2242 cm$^{-1}$. The $^1$H-NMR absorption spectrum of the compound measured in heavy chloroform CDCl$_3$ as the solvent had peaks of the δ value at 1.48 ppm, 2.05 to 2.10 ppm, 2.70 ppm, 3.70 ppm and 6.80 ppm. These results supported the identification that the product was the above mentioned compound. Further, the ultraviolet absorption spectrum of the compound was measured in propyleneglycol monomethyl ether as the solvent to detect an absorption band having a peak wavelength at 280 nm with a molar absorption coefficient of ε=7090. The molar absorption coefficient at a wavelength of 248 nm was 1500.

EXAMPLE 4

α-(Isopropylsulfonyloxyimino)-1-cyclopentenyl acetonitrile having a melting point of 88° C. was prepared in substantially the same manner as in Example 1 excepting replacement of the mesyl chloride with the same molar amount of isopropylsulfonyl chloride.

The infrared absorption spectrum of this product compound had absorption bands with peaks at wave numbers of 894 cm$^{-1}$, 970 cm$^{-1}$, 1377 cm$^{-1}$, 1610 cm$^{-1}$ and 2243 cm$^{-1}$. The $^1$H-NMR absorption spectrum of the compound measured in heavy chloroform CDCl$_3$ as the solvent had peaks of the δ value at 1.35 ppm, 1.50 ppm, 2.05 to 2.10 ppm, 2.70 ppm, 3.23 ppm and 6.80 ppm. These results supported the identification that the product was the above mentioned compound. Further, the ultraviolet absorption spectrum of the compound was measured in propyleneglycol monomethyl ether as the solvent to detect an absorption band having a peak wavelength at 281 nm with a molar absorption coefficient of ε=7200. The molar absorption coefficient at a wavelength of 248 nm was 1650.

EXAMPLE 5

α-(n-Butylsulfonyloxyimino)-1-cyclopentenyl acetonitrile having a melting point of 73° C. was prepared in substantially the same manner as in Example 1 excepting replacement of the mesyl chloride with the same molar amount of n-butylsulfonyl chloride.

The infrared absorption spectrum of this product compound had absorption bands with peaks at wave numbers of 894 cm$^{-1}$, 970 cm$^{-1}$, 1377 cm$^{-1}$, 1610 cm$^{-1}$ and 2242 cm$^{-1}$. The $^1$H-NMR absorption spectrum of the compound measured in heavy chloroform CDCl$_3$ as the solvent had peaks of the δ value at 0.97 ppm, 1.53 ppm, 1.92 ppm, 2.05 to 2.10 ppm, 2.70 ppm, 3.65 ppm and 6.80 ppm. These results supported the identification that the product was the above mentioned compound. Further, the ultraviolet absorption spectrum of the compound was measured in propyleneglycol monomethyl ether as the solvent to detect an absorption band having a peak wavelength at 280 nm with a molar absorption coefficient of ε=7300. The molar absorption coefficient at a wavelength of 248 nm was 1600.

EXAMPLE 6

α-(Ethylsulfonyloxyimino)-1-cyclohexenyl acetonitrile having a melting point of 70° C. was prepared in substantially the same manner as in Example 2 excepting replacement of the mesyl chloride with the same molar amount of ethanesulfonyl chloride.

The infrared absorption spectrum of this product compound had absorption bands with peaks at wave numbers of 840 cm$^{-1}$, 1189 cm$^{-1}$, 1380 cm$^{-1}$, 1629 cm$^{-1}$ and 2240 cm$^{-1}$. The $^1$H-NMR absorption spectrum of the compound measured in heavy chloroform CDCl$_3$ as the solvent had peaks of the δ value at 1.48 ppm, 1.70 ppm, 2.35 ppm, 3.70 ppm and 6.90 ppm. These results supported the identification that the product was the above mentioned compound. Further, the ultraviolet absorption spectrum of the compound was measured in propyleneglycol monomethyl ether as the solvent to detect an absorption band having a peak wavelength at 273 nm with a molar absorption coefficient of ε=11600. The molar absorption coefficient at a wavelength of 248 nm was 2600.

EXAMPLE 7

α-(Isopropylsulfonyloxyimino)-1-cyclohexenyl acetonitrile having a melting point of 71° C. was prepared in substantially the same manner as in Example 2 excepting replacement of the mesyl chloride with the same molar amount of isopropylsulfonyl chloride.

The infrared absorption spectrum of this product compound had absorption bands with peaks at wave numbers of 840 cm$^{-1}$, 1189 cm$^{-1}$, 1380 cm$^{-1}$, 1630 cm$^{-1}$ and 2241 cm$^{-1}$. The $^1$H-NMR absorption spectrum of the compound measured in heavy chloroform CDCl$_3$ as the solvent had peaks of the δ value at 1.35 ppm, 1.48 ppm, 1.50 ppm, 1.70 ppm, 2.35 ppm, 3.23 ppm and 6.90 ppm. These results supported the identification that the product was the above mentioned compound. Further, the ultraviolet absorption spectrum of the compound was measured in propyleneglycol monomethyl ether as the solvent to detect an absorption band having a peak wavelength at 273 nm with a molar absorption coefficient of ε=10000. The molar absorption coefficient at a wavelength of 248 nm was 2000.

EXAMPLE 8

α-(n-Butylsulfonyloxyimino)-1-cyclohexenyl acetonitrile having a melting point of 65° C. was prepared in substantially the same manner as in Example 2 excepting replacement of the mesyl chloride with the same molar amount of n-butylsulfonyl chloride.

The infrared absorption spectrum of this product compound had absorption bands with peaks at wave numbers of 840 cm$^{-1}$, 1190 cm$^{-1}$, 1380 cm$^{-1}$, 1629 cm$^{-1}$ and 2240 cm$^{-1}$. The $^1$H-NMR absorption spectrum of the compound measured in heavy chloroform CDCl$_3$ as the solvent had peaks of the δ value at 0.97 ppm, 1.53 ppm, 1.70 ppm, 1.92 ppm, 2.35 ppm, 3.65 ppm and 6.90 ppm. These results supported the identification that the product was the above mentioned compound. Further, the ultraviolet absorption spectrum of the compound was measured in propyleneglycol monomethyl ether as the solvent to detect an absorption band having a peak wavelength at 274 nm with a molar absorption coefficient of ε=9000. The molar absorption coefficient at a wavelength of 248 nm was 2100.

What is claimed is:

1. A non-aromatic cyanooxime sulfonate compound represented by the general formula

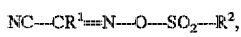

$$NC-CR^1=N-O-SO_2-R^2,$$

in which $R^1$ and $R^2$ are, each independently from the other, an unsubstituted or halogen-substituted monovalent aliphatic hydrocarbon group selected from the group consisting of alkyl, cycloalkyl, alkenyl and cycloalkenyl groups.

2. The non-aromatic cyanooxime sulfonate compound as claimed in claim 1 in which the groups denoted by $R^1$ and $R^2$ in the general formula are, each independently from the other, an unsubstituted monovalent aliphatic hydrocarbon group selected from the group consisting of alkyl, cycloalkyl, alkenyl and cycloalkenyl groups.

3. The non-aromatic cyanooxime sulfonate compound as claimed in claim 2 in which the group denoted by $R^1$ in the general formula is a cycloalkenyl group.

4. The non-aromatic cyanooxime sulfonate compound as claimed in claim 3 in which the cycloalkenyl group is 1-cyclopentenyl group or 1-cyclohexenyl group.

5. The non-aromatic cyanooxime sulfonate compound as claimed in claim 2 in which the group denoted by $R^2$ is an alkyl group.

6. The non-aromatic cyanooxime sulfonate compound as claimed in claim 5 in which the alkyl group has 1 to 4 carbon atoms.

* * * * *